(12) United States Patent
Keita et al.

(10) Patent No.: US 9,980,638 B2
(45) Date of Patent: May 29, 2018

(54) SYSTEMS AND METHODS FOR MEASURING REFRACTIVE ERROR AND OPHTHALMIC LENSES PROVIDED THEREFROM

(71) Applicant: ESSILOR INTERNATIONAL (Compagnie Generale d'Optique), Charenton-le-Pont (FR)

(72) Inventors: Gabriel Keita, Dallas, TX (US); Howard Purcell, Dallas, TX (US)

(73) Assignee: ESSILOR INTERNATIONAL (Compagnie Generale d'Optique), Charenton-le-Pont (FR)

( * ) Notice: Subject to any disclaimer, the term of this patent is extended or adjusted under 35 U.S.C. 154(b) by 0 days. days.

(21) Appl. No.: 15/309,862

(22) PCT Filed: Nov. 20, 2014

(86) PCT No.: PCT/IB2014/003037
§ 371 (c)(1),
(2) Date: Nov. 9, 2016

(87) PCT Pub. No.: WO2015/173605
PCT Pub. Date: Nov. 19, 2015

(65) Prior Publication Data
US 2017/0265738 A1   Sep. 21, 2017

Related U.S. Application Data

(60) Provisional application No. 61/992,000, filed on May 12, 2014.

(51) Int. Cl.
*A61B 3/02*   (2006.01)
*A61B 3/028*   (2006.01)
(Continued)

(52) U.S. Cl.
CPC ............ *A61B 3/028* (2013.01); *A61B 3/0033* (2013.01); *A61B 3/103* (2013.01); *A61B 3/1015* (2013.01); *G02C 7/027* (2013.01)

(58) Field of Classification Search
CPC ......... A61B 3/032; A61B 3/18; A61B 3/0033; A61B 3/024; A61B 3/028
(Continued)

(56) References Cited

U.S. PATENT DOCUMENTS 4,806,010 A   2/1989   Ewer et al.
5,187,505 A   2/1993   Spector
(Continued)

FOREIGN PATENT DOCUMENTS

EP   0 225 034 A1   6/1987
WO   2004/072687 A2   8/2004

OTHER PUBLICATIONS

International Search Report and Written Opinion dated Jun. 15, 2015 in PCT/IB2014/003037 filed Nov. 20, 2014.

*Primary Examiner* — Mohammed Hasan
(74) *Attorney, Agent, or Firm* — Oblon, McClelland, Maier & Neustadt, L.L.P.

(57) ABSTRACT

Systems and methods for providing identification factors for an individual wearer. Some or all of the identification factors when within a predetermined value provide a prescription and corrective ophthalmic lenses for a selected individual wearer, the corrective ophthalmic lens having at least one correction that is to the nearest 0.20 diopter, or is in a range between about the nearest 0.01 diopter and about the nearest 0.20 diopter. The prescription and corrective ophthalmic lenses are obtained by at least first analysis performed with a first instrument, a second analysis performed with a second
(Continued)

instrument, and a third analysis performed with a third instrument, in which each instrument is different, and each analysis is different.

14 Claims, 5 Drawing Sheets

(51) Int. Cl.
    *A61B 3/00*     (2006.01)
    *A61B 3/10*     (2006.01)
    *A61B 3/103*     (2006.01)
    *G02C 7/02*     (2006.01)

(58) Field of Classification Search
    USPC ................................................ 351/200–246
    See application file for complete search history.

(56) References Cited

U.S. PATENT DOCUMENTS

| | | | |
|---|---|---|---|
| 2004/0156021 A1* | 8/2004 | Blum | A61B 3/0285 351/233 |
| 2007/0195264 A1* | 8/2007 | Lai | A61B 3/0285 351/159.78 |
| 2010/0265463 A1 | 10/2010 | Lai | |
| 2012/0307194 A1 | 12/2012 | Croft et al. | |

* cited by examiner

SYSTEMS AND METHODS FOR MEASURING REFRACTIVE ERROR AND OPHTHALMIC LENSES PROVIDED THEREFROM

CROSS-REFERENCE TO RELATED APPLICATIONS

This Application claims the benefit of priority to U.S. Provisional Appl. No. 61/992,000 filed May 12, 2014, the entirety of which is herein incorporated by reference.

TECHNICAL FIELD

The invention described relates to systems and methods for providing high resolution corrective ophthalmic lenses. The systems and methods include making measurements and providing corrective ophthalmic lenses based on a recognition of certain measurements.

BACKGROUND

Correction of ocular vision by nonsurgical means involves measuring refractive error using gradations in steps of ¼ or 0.25 diopter. Such gradations do not account for accuracy levels now available with a digital apparatus. Thus, there remains a need to provide gradations that are better than 0.25 diopter. However, such higher level gradations, when provided on the surface of an ophthalmic lens, one used for correction of ocular vision, are not readily apparent to many individuals, particularly those with reduced sensitivity to higher level gradations. In these individuals with reduced sensitivity or even an inability to perceive higher level gradations, a correction of higher resolution (a resolution that is less than 0.25 diopter) may not be appreciated or even perceived. On the other hand, other, more sensitive and/or discerning wearers may perceive and/or appreciate corrections, and hence lenses with resolutions that are less than 0.25 diopter. There remains a need to identify such individualized wearers having a higher sensitivity, those that are more discerning, capable of benefiting from a higher degree of lens precision than is currently being provided by traditional methods of evaluating an individual wearer, and as currently being provided by traditional methods of manufacturing and dispensing a corrective lens for the wearer.

Described herein are systems and methods that address one or more of the above identified issues, in order to provide corrective three-dimensional ophthalmic lenses for one or more particular individualized wearers.

SUMMARY

Disclosed herein are methods for determining refraction and for providing wearer-specific corrective ophthalmic lenses to a particular individualized wearer. In one or more embodiments, the particular individualized wearer is one selected as having identification factors that are considered to be associated with an ability to perceive and recognize finer gradation changes on a surface of an ophthalmic lens used for correction of ocular vision. The identification factors are identified upon making measurements using finer gradation changes, some of which are at least double the standard level for measuring such gradations. In one or more embodiments, the gradation step is at least about 0.125 or less, or may be at least about 0.12 diopter or less. In some embodiments, the increment is between about 0.01 to about 0.17 diopter. In other embodiments, the increment is between about 0.01 to about 0.20 diopter. In one or more embodiments, the finer gradation step or increment translates to an improvement on the surface of the ophthalmic lens, and hence, an improvement in the overall level of correction of an ophthalmic lens for the particular individualized wearer. With methods and systems described herein, measured visual performance of a lens prepared and prescribed as disclosed herein will be better, or superior, to the measured visual performance of a lens prepared and prescribed using a traditional method of providing a gradation step that is to the nearest 0.25 diopter. With methods and systems described herein, subjective visual acceptance of a lens prepared and prescribed as disclosed herein will be better, or superior, to the subjective visual acceptance of a lens prepared and prescribed using a traditional method of providing a gradation step that is to the nearest 0.25 diopter.

Generally, the particular individual wearer is one considered capable of identifying the finer gradation change. Each individual wearer is determined and recognized through an analysis of a plurality of identification factors. The identification factors include at least a first identification factor and a second identification factor and generally also include a third identification factor and may also include a fourth identification factor. In one or more embodiments, each identification factor must be at or within a predetermined value. In some embodiments, only an individual wearer determined to have a first identification factor and a second identification factor that are each at or within a predetermined value is selected. In some embodiments, only an individual wearer determined to have a first identification factor and a second identification factor and a third identification factor that are each at or within a predetermined value is selected. In further embodiments, only an individual wearer determined to have a first identification factor and a second identification factor and a third identification factor that are all at or within a predetermined value and who successfully recognizes a fourth identification factor that is at or within a predetermined value is selected and/or found to be successful.

In one or more embodiments, at least one identification factor is determined by analysis of the individual. The analysis may be a personality analysis, an optometer analysis, a visual analysis and various combinations thereof.

Another identification factor is determined by at least an objective evaluation. The objective evaluation includes identification of the ocular wavefront. In one or more embodiments, the objective evaluation is performed by an aberrometer. The aberrometer may include any clinical or optical aberrometer measuring either ingoing or outgoing light. The objective evaluation is typically a bilateral evaluation (performed in each eye, not necessarily at the same time). The objective evaluation includes evaluations of differences in aberrations expressed as root mean square (RMS) wavefront errors. In a first embodiment, only an individual wearer presenting with an identification factor that is an RMS of about 0.3 diopter or lower, or 0.2 diopter or lower, or lower than 0.2 diopter in both eyes is selected. In an additional embodiment, an individual wearer presenting with an identification factor that is an RMS of less than about 0.47 in each eye, or with a identification factor that is an RMS of less than about 0.47 in each eye and/or comatic aberration (coma) less than 0.20 in each eye, is allowed to proceed with a subjective evaluation described below, which may be useful for manufacturing and dispensing a corrective lens as described herein.

Another identification factor is generally included in the described method. This identification factor is identified using a subjective evaluation, which measures visual acuity (e.g., uncorrected distance, corrected distance, high and/or low contrast, pinhole test, and/or near vision test). The subjective evaluation is typically a bilateral evaluation (performed in each eye, not necessarily at the same time). The subjective evaluation measures refractive changes using gradations in steps of at least 0.125 diopter. The subjective evaluation may also measure refractive changes using gradations in steps of about or less than about 0.125 diopter. Only an individual wearer presenting with this identification factor, that is an ability to recognize refraction changes using gradations in steps of at least 0.125 diopter in both eyes, or about or less than 0.125 diopter, is selected.

In the embodiments described herein, systems and methods are described for recognizing identification factors in order to provide higher order corrective ophthalmic lenses, (also referred to interchangeably herein as higher resolution corrective ophthalmic lenses), specific to the individual wearer. The higher order corrective ophthalmic lenses are provided to the individual wearer based on at least some of the individual measurements obtained.

Upon obtaining the higher order corrective ophthalmic lenses, another identification factor includes recognition of one or more identifiers on a reading card with the higher order corrective ophthalmic lenses. In some embodiments, one or more reading cards are used, typically located at a reading distance. The one or more reading cards may be designed for contrast sensitivity and/or color sensitivity evaluation. Only an individual wearer presenting with this identification factor, that is an ability to recognize contrast sensitivity and/or color sensitivity in one or more reading cards, when the selected wearer is using a newly prepared higher order corrective ophthalmic lens (having a higher level of resolution, that is a finer or higher resolution than the traditional resolution, which is only to the nearest 0.25 diopter) as compared with using a previous corrective ophthalmic lens (having a traditional resolution only to the nearest 0.25 diopter), is selected.

Several benefits arise from the embodiments described herein including providing wearer-specific higher order corrective ophthalmic lenses to a selected wearer, providing increased visual clarity, contrast sensitivity and/or color sensitivity in the higher order corrective ophthalmic lenses when provided to the selected wearer, and providing improved overall refraction, and improved visual acuity by refraction. Economic benefits with improved quality of care as well as quality of life will also be provided by the methods and by the higher order corrective ophthalmic lenses described herein.

In one or more embodiments, described herein are methods for evaluating the corrective needs of a wearer and for providing a corrective ophthalmic lens to a selected individual wearer. Such a method comprises using a first instrument, identifying in a first analysis a first identification factor from a plurality of parameters for evaluating an individual wearers' level of perception and control. In various embodiments, the first identification factor is associated with having self confidence and organizational skills. The method further comprises using a second instrument, identifying in a second analysis a second identification factor, wherein the second instrument includes equipment for objectively measuring refractive error in an eye, wherein the second analysis is performed when the first identification factor is within a predetermined value. Using a third instrument, identifying in a third analysis a third identification factor, wherein the third instrument includes equipment for subjectively evaluating refraction in an eye and refraction is evaluated using an incremental change that is lower than 0.20 diopter, or is in a range between about the nearest 0.01 diopter and about the nearest 0.20 diopter, wherein the third analysis is performed when the second identification factor is within a predetermined value. In various embodiments, the method additionally comprises generating a prescription based on the refraction obtained from at least one of the second instrument and the third instrument, wherein the prescription includes at least one correction that is to the nearest 0.20 diopter, or is in a range between about the nearest 0.01 diopter and about the nearest 0.20 diopter. The plurality of parameters may include questions provided in a questionnaire. In the methods, some of the steps may be automated. In some embodiments, the refractive error is one or more of a total root mean square of at least about 0.3 diopter or less in each eye and at least about 0.2 diopter or less in each eye. The refractive error is generally measured using a wavefront aberrometer. In various embodiments, the second identification factor of the wearer is identified when the wearer presents a difference between auto refraction and wavefront refraction that is (i) equal to or less than 0.5 diopter sphere or equal to or less than 0.5 diopter cylinder and (ii) equal to or less than 10 degree axis. The method may further comprise a fourth identification factor obtained by providing a fourth analysis on the wearer after dispensing the corrective ophthalmic lens, the fourth analysis including a visual acuity assessment. In various other embodiments, the fourth analysis includes a comparison of vision when wearing the corrective ophthalmic lens as compared with vision when wearing a corrective lens used previously by the wearer.

In additional embodiments are described a method of evaluation for a wearer in need of a corrective ophthalmic lens, the method comprising defining a first identification factor of the wearer from a plurality of perception parameters that identify personal perception and control. The method further comprises defining aberrations in the eyes of the wearer using a wavefront aberrometer when the first identification factor of the wearer is within a predetermined value. The method further comprises defining a second identification factor of the wearer, using subjective refraction with an incremental change that is or is in a range between about the nearest 0.01 diopter and about the nearest 0.17 diopter, when the first identification factor is a total root mean square value lower than 0.3 diopter in each eye. In additional embodiments, the method further comprises preparing the corrective ophthalmic lens for the wearer when the second identification factor of the wearer includes perceiving the incremental change that is or is in a range between about the nearest 0.01 diopter and about the nearest 0.17 diopter. Still further, the method may comprise evaluating the corrective ophthalmic lens on the wearer after dispensing the corrective ophthalmic lens by comparing vision of the wearer when using the corrective ophthalmic lens as compared with vision when using a corrective lens used previously by the wearer. The second identification factor of the wearer involves perceiving the incremental change that is at least about 0.12 diopter or less. The first identification factor is associated with having self confidence and organizational skills. Defining aberrations in the eyes of the wearer using a wavefront aberrometer may occur in wearers presenting a difference between auto refraction and wavefront refraction that is (i) equal to or less than 0.5 diopter sphere or equal to or less than 0.5 diopter cylinder and (ii) equal to or less than 10 degree axis.

Also described herein is a system for evaluating a wearer in need of a corrective ophthalmic lens, the system comprising a kiosk for measuring personal perception and control of the wearer, the kiosk also capable of providing information about the personal perception and control of the wearer. The system also includes equipment for objectively measuring a wavefront of each eye of the wearer and for providing information about the wavefront. In one or more embodiments, the equipment for objectively measuring a wavefront may be an aberrometer. The system also includes a subjective refraction analyzer for measuring subjectively refraction in each eye of the wearer and for providing information about the refraction, wherein the measuring includes an incremental change that is or is in a range between about the nearest 0.01 diopter and about the nearest 0.20 diopter. In one or more embodiments, the system determines that a wearer is in need of the corrective ophthalmic lens when the information about the personal perception and control of the wearer indicates the wearer as having one or more of self confidence and organizational skills, and when the information about the wavefront provides a total root mean square value of 0.3 diopter or less, and when the information about the refraction indicates the wearer as perceiving the incremental change that is lower than 0.20 diopter, or is in a range between about the nearest 0.01 diopter and about the nearest 0.20 diopter. In the system, one or more of the kiosk, aberrometer and subjective refraction analyzer may be operably linked.

Also described is a method for evaluation of a wearer in need of a corrective ophthalmic lens, the method comprising defining a first identification factor of the wearer by a first instrument that includes a plurality of control parameters to evaluate the wearers' level of perception and control. The method further comprises defining a second identification factor of the wearer with a second instrument when the first identification factor of the wearer is within a predetermined value, wherein the second instrument is a wavefront aberrometer for identifying aberrations in the eyes of the wearer. The method may further comprise defining a third identification factor of the wearer with a third instrument when the second identification factor is a total root mean square value lower than 0.3 diopter in each eye, wherein the third instrument measures subjective refraction in each eye with an incremental change that is lower than 0.20 diopter, or is in a range between about the nearest 0.01 diopter and about the nearest 0.20 diopter. In some embodiments, the method further comprises preparing a prescription in accordance with measurements obtained from the third analysis, in which the prescription includes the incremental change that are lower than 0.20 diopter, or in a range between about the nearest 0.01 diopter and about the nearest 0.20 diopter. In various other embodiments, the method further comprises evaluating vision of the wearer after defining the third identification factor. In other embodiments, the incremental change is at least about 0.12 diopter or less.

Additionally described is a method of determining suitability of a wearer for enhanced corrective ophthalmic lens, the method comprising providing a first analysis to a wearer using a first instrument to identify a first identification factor from a plurality of parameters related to personal perception and control of a wearer. The method further comprises determining a sensitivity factor for the wearer, the sensitivity factor being indicative of the wearer's ability to perceive a change lower than 0.25 diopter, where the higher the sensitivity factor, the more suitable a wearer is for an enhanced corrective ophthalmic lens. In various embodiments, the first instrument comprises a wavefront aberrometer or an autorefractor. In other embodiments, in response to the first identification factor or the second identification factor being indicative of a wearer suitable for the enhanced corrective ophthalmic lens, the method further comprises providing a third analysis for subjectively evaluating refraction in an eye. In some embodiments, the plurality of parameters is related to a pupil diameter of the wearer.

Additional details relating to the various embodiments of the invention will be further described in the detailed description.

BRIEF DESCRIPTION OF THE DRAWINGS

Various inventive features described herein are set forth with particularity in the appended claims. A better understanding of various features and advantages described herein will be obtained by reference to the following detailed description that sets forth illustrative embodiments and the accompanying drawings of which:

DETAILED DESCRIPTION

Figure 1:
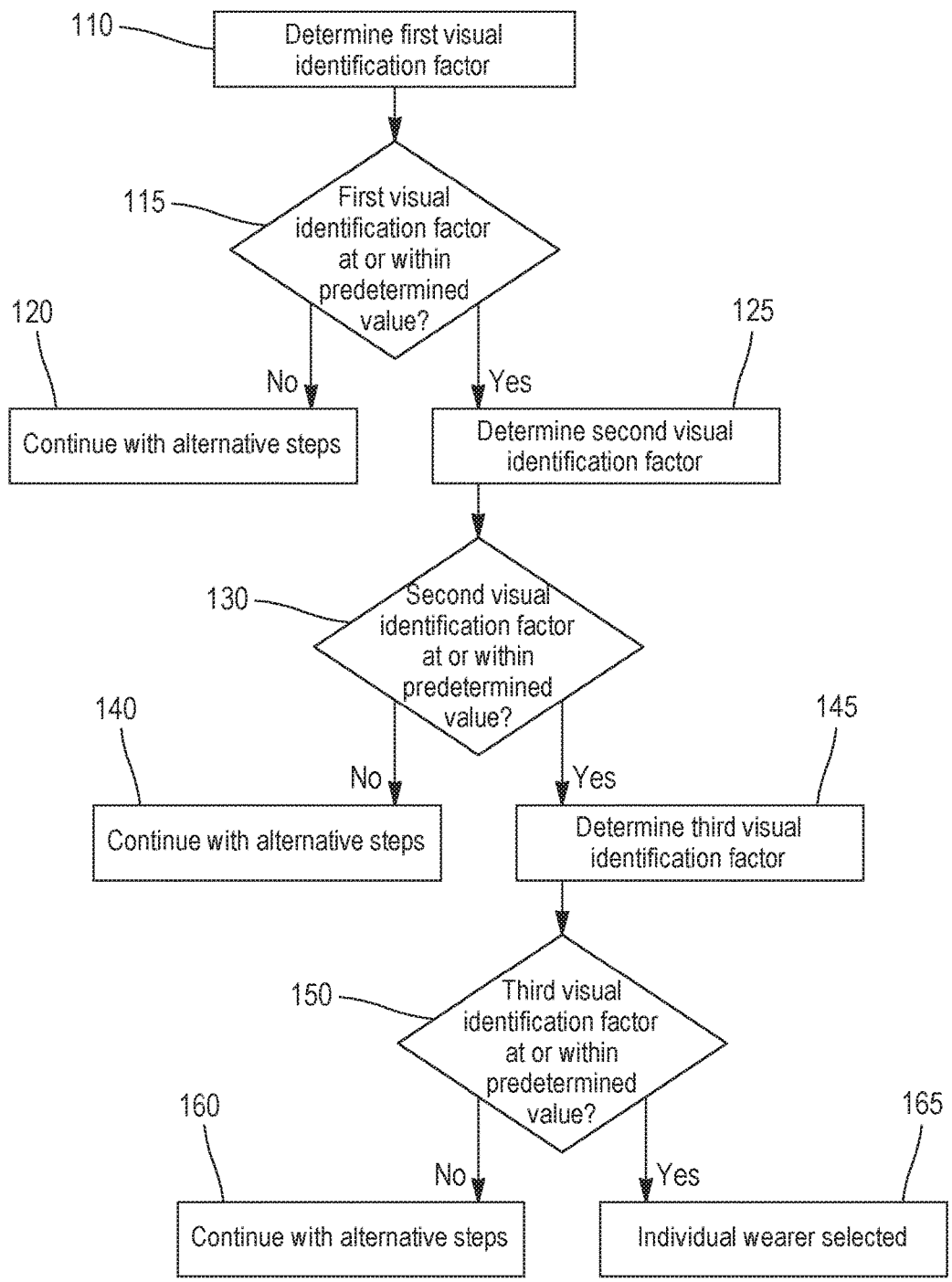
FIG. 1 illustrates a representative method of identifying identification factors and selecting an individual wearer as described herein.

Described herein are methods for determining a plurality of identification factors in an individual wearer and for selection of an individual wearer. Identification factors are identified and an individual wearer is selected as depicted in FIG. 1. In block 110, a first identification factor is identified. The first visual identification is then determined to be at or within a predetermined value at block 115. If the first identification factor is not at or within a predetermined value, the individual wearer is not selected and an alternative arrangement for the individual wearer is provided at block 120, such as any alternative steps known for correcting the wearer's vision. In some embodiments, the individual wearer at block 120 may still be evaluated for and dispensed a higher order corrective ophthalmic lenses as described below.

If the first identification factor is at or within a predetermined value at block 125, a second identification factor is identified at block 130. If the second identification factor is not at or within a predetermined value, the individual wearer is not selected and an alternative arrangement for the individual wearer is provided at block 140, such as any alternative steps for correcting the wearer's vision. In some embodiments, the individual wearer at block 140 may still be evaluated for and dispensed a higher order corrective ophthalmic lenses as described below. If the second identification factor is at or within a predetermined value at block 145, a third identification factor is identified at block 150. If the third identification factor is not at or within a predetermined value, the individual wearer is not selected and an alternative arrangement for the individual wearer is provided at block 160, such as any alternative steps for correcting the wearer's vision. In some embodiments, the individual wearer at block 160 may still be evaluated for and dispensed a higher order corrective ophthalmic lenses as described below. If the third identification factor is at or within a predetermined value, an individual wearer is selected at block 165. The selected individual wearer at block 165 will be dispensed a higher order corrective ophthalmic lenses as described below. At least one of the identification factors and/or its accompanying measurements, with or without additional evaluation data, will be used to dispense the higher order corrective ophthalmic lenses at the higher level of resolution as is described herein. Accordingly, the described methods contrast with the traditional refraction methods that have been carried out to the nearest 0.25 diopter in order to dispense at the same (low order) resolution.

In one or more embodiments, a first identification factor is determined first, a second identification factor is determined second, and a third identification factor is determined third. In alternative embodiments, other arrangements, and hence evaluations and determinations, of any of the first, second and/or third identification factor may be performed. A combination of recognizing at least a first identification factor at or within a predetermined value, along with recognizing either or both a second identification factor and/or a third identification factor have been found herein to be preferred for appropriate selection of an individual wearer as described herein, and for providing a higher order (higher resolution) corrective lens for the selected individual wearer, one who recognizes the higher order corrective lens, and is more sensitive and/or discerning so as to perceive and/or appreciate the higher order corrections.

For the purposes described herein, identification factors are identified as a first identification factor, a second identification factor, a third identification factor, and a fourth identification factor. Yet, the prefix "first," "second," "third," and "fourth" are generally considered interchangeable in their order and timing.

For identifying a first identification factor, a first analysis of an individual wearer will be performed. The first analysis may include a visual perception analysis, a personality analysis, a visual acuity analysis and/or an optometer analysis. The analysis is generally constructed to assess at least a tolerance to blur, a heightened level of visual perception, and/or a measure of visual sensitivity, such as a sensitivity to blur, which may or may not include an analysis of visual acuity. Generally, the first analysis is one that can be performed by the individual wearer, or by an optometrist, an assistant in an optometrist's office. Preferably, the first analysis is one that can be performed in a short period of time, such that it is performed in less than about one hour, or less than about thirty minutes, or less than about 20 minutes, or less than about 15 minutes, or less than about 10 minutes, or less than 5 minutes. In one or more embodiments, the analysis is one that can be performed with the assistance of a computer/processor 210 (FIG. 2), such that all or at least a portion of the first analysis may be performed or conducted with a computer/processor, and all or at least a portion of data obtained from the analysis can be gathered, calculated, transformed, retrieved and/or stored on a computer/processor.

In one example, the first analysis is a type of perception test. An example of a first analysis is one that has been used to identify a wearer's tolerance to changes in vision, such as blur, and/or to changes in induced blur. In one embodiment, the first analysis may include an evaluation of personal perceptions, such as an evaluation of their personality (e.g., confidence, control and manner of organization), an evaluation of their response to social and/or emotional issues, an evaluation of the response to induced blur, and some combination thereof. The evaluation may be in the form of a questionnaire, with or without images. The number of questions may vary. In some embodiments, a format includes at or about four questions, or more than four questions, or may include five or more questions, or up to about ten questions, or up to about twenty questions. The questions may include items that have been found to have a higher correlation with blur tolerance (e.g., confidence and organization; see, e.g., Woods, et al., Invest. Ophthal. Visual Sci. 2010; 51(11): 6077-6082). The items may be related to personal expectations, organizational standards, social patterns, cleanliness, visual perception, visual clarity, and/or tension/anxiety of the individual wearer, as examples. At least some of the questions may be directed to personal perceptions. Additional questions may also be included in the first analysis to obtain further information about the individual wearer (e.g., age, medications, other ocular complications, recent ocular changes, number years as a wearer, etc.). One representative list of items for a first analysis is provided in TABLE 1.

TABLE 1

I usually have doubts about the simple everyday things I do.
I never felt like I could meet my parents' expectations.
If I fail partly, it is as bad as being a complete failure.
If I don't set the highest standards for myself, I am likely to end up a second-rate person.
I tend to get behind in my work because I repeat everything over and over.
I sometimes get myself into a state of tension and turmoil as I think of the day's events.
I rarely feel fearful or anxious.
I never seem to be able to get organized.
I am an organized person.
I keep my belongings clean and neat.
I am fastidious, meticulous, careful, and precise.
I have social poise and presence; socially at ease.
Is verbally fluent.
Enjoys sensuous experiences.
Other people seem to accept lower standards from themselves than I do.

For a test that includes items, such as those listed in TABLE 1, the items are provided a value between 1 and 9 by the individual wearer, and the values are then scored based on a weight. An example of a questionnaire described herein that takes some of the items listed in TABLE 1 and provides a normalized score is provided in TABLE 2, in which the weight (i) was previously identified. From the scoring, a first identification factor is obtained using formula (1).

First identification factor=$\Sigma$[Normalized score($i$)× Weight($i$)]     (1)

With the above formula, (i) is a whole number from 1 to x, wherein x is the number of questions used in the analysis. With examples provided in TABLE 2 and upon using equation (1) in combination with TABLE 2, a predetermined value that is at or below about 3.5 has been identified for selecting an individual wearer, when using a first analysis of the type which is a perception test, such as one depicted in TABLE 2. The predetermined value may, in some embodiments, be one that indicates a higher level of personal perception and control, as compared with those with lesser perception and need to control (e.g., lacking confidence).

The predetermined value may also be one that indicates an individual wearer as one exhibiting or having one or more of higher personal expectations, higher organizational standards, higher personal control or control of surroundings, higher perception of and the following of social patterns, higher level of cleanliness, higher visual perception, higher visual clarity, higher confidence, and/or higher tension/anxiety. The predetermined value is, thus, associated with a higher degree of control and/or a higher perception of induced blur by the individual wearer.

TABLE 2

| Representative Questionnaire | Normalized score (i) | Weight (i) |
|---|---|---|
| I usually have doubts about the simple everyday things I do. | (score) | 0.56 |
| I never felt like I could meet my parents' expectations. | (score-5)/4 | 0.76 |
| If I fail partly, it is as bad as being a complete failure. | (score) | 0.65 |
| If I don't set the highest standards for myself, I am likely to end up a second-rate person. | (score-5)/4 | 0.51 |
| I tend to get behind in my work because I repeat everything over and over. | (score-5)/4 | 0.59 |
| I sometimes get myself into a state of tension and turmoil as I think of the day's events. | (score-5)/4 | 0.42 |
| I rarely feel fearful or anxious. | (score-5)/4 | 0.35 |
| I never seem to be able to get organized. | (score-5)/4 | 0.76 |
| I am an organized person. | (score-5)/4 | −0.86 |
| I keep my belongings clean and neat. | (score-5)/4 | −0.79 |
| I am fastidious, meticulous, careful, and precise. | (score-5)/4 | −0.44 |
| I have social poise and presence; socially at ease. | (score-5)/4 | −0.37 |

Thus, when the first analysis is a perception test such as or in a manner as represented by the test identified in TABLE 2, a first identification value is identified upon completion of the first analysis by performing the steps outlined above and using formula (1). From the first identification value, an individual wearer is selected that provides a first identification value at or within the predetermined value for the first analysis (e.g., identified as a wearer having higher degree of control and/or a higher perception of induced blur).

Figure 6:
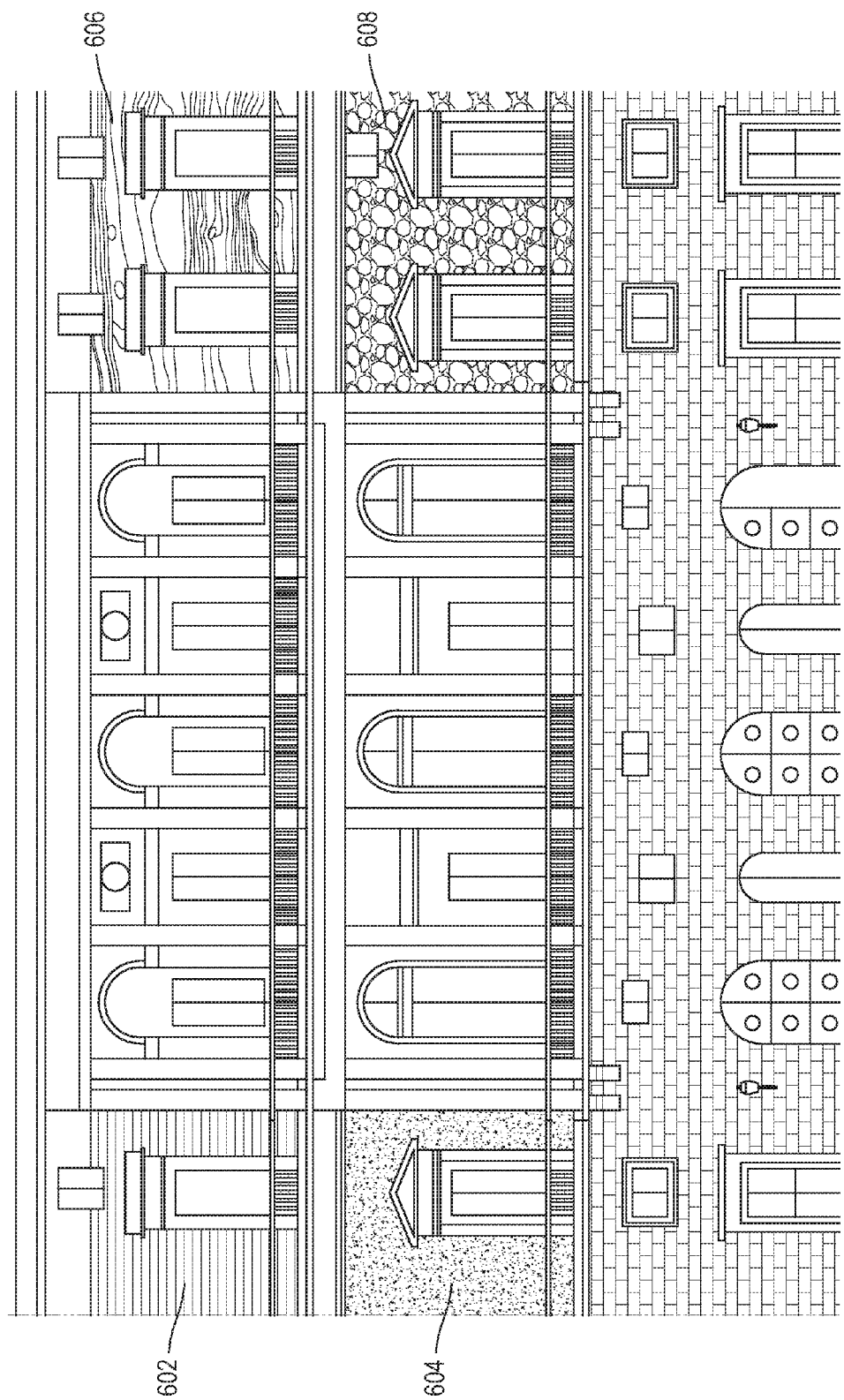
FIG. 6 depicts additional representative objects and/or reading cards for analyzing an individual's quality of vision as described herein.

For identifying a first identification factor, a first analysis of the wearer may also include an analysis of visual acuity and/or other modes of identifying visual perception and/or perception of blur. For example, the analysis may be one that identifies a recognition of one or more blurred objects, or a recognition of finer details in one or more objects, and/or a recognition of differences between two objects having differences in blur or differences in fine details and/or differences in color details. A representative example of objects, including finer objects useful for assessing a first identification factor is depicted in FIG. 6 and described in greater detail below. In some embodiments, a first analysis may also include an analysis of visual acuity, which provides a level of visual performance, in which a predetermined value is also associated with good visual acuity. This predetermined value may include values associated with good visual clarity, and good perception of contrast, sharpness and/or color. In some embodiments, a first analysis may also include an analysis of visual acuity in combination with an analysis of visual recognition of visual changes (e.g., of objects, details, blur, and/or color), in which a predetermined value includes values associated with good visual acuity and good visual recognition of visual changes. In some embodiments, a combination of visual acuity, visual recognition and perception of personal performance may be used as a first analysis, in which a predetermined value is associated with the perception test (as described above) in which a wearer exhibits a higher level of personal perception and control, as well as values associated with good visual acuity and good visual recognition of visual changes.

In some embodiments, the first analysis or perception analysis includes queries provided only as questions, only as statements, only as a selection of images, or as some combination of questions, statements and/or images. In some embodiments, the queries are modified for each test. The modification may be predetermined or random. Whether predetermined or random, one or a number of modifications to the queries that may be performed include but are not limited to: addition of a query, deletion of query, a query having multiple forms (e.g., minor changes in the wording of a question or minor changes in the visual image or a changes in selection from one of a plurality of queries and/or images designated to have a same or similar value or feature), a change in the format of the query, and a change in the order of the query. The queries may be provided by a person or by a device, including a device having a processor and the ability to record, store and/or change the queries in either the predetermined or random manor. Recording of the response to queries may be made by a person or by a device, including a device having a processor and the ability to record, store and/or transform the response. In some embodiments, the queries are automated.

Figure 2:
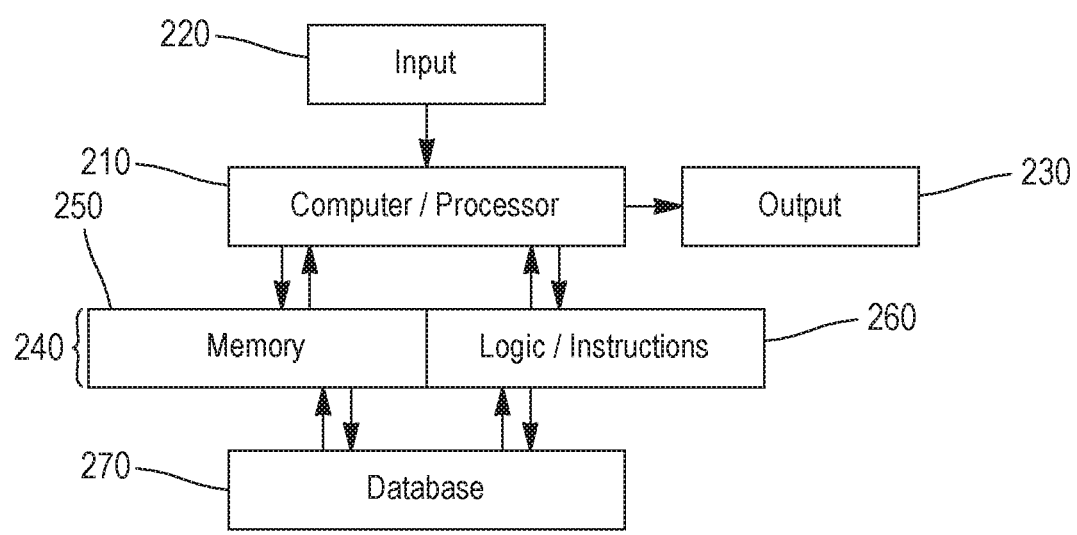
FIG. 2 illustrates a representative means for identifying identification factors and selecting an individual wearer providing steps of the one or more methods as described herein.

In some embodiments, the first analysis or perception analysis is in written form. In some embodiments the first or visual perception analysis or at least a portion thereof is on paper. In some embodiments at least a portion thereof is on a computer program product comprising a non-transitory computer readable medium 240 having computer program logic/instructions 260 encoded thereon for enabling a processor 210 to perform some or all of the analysis, as illustrated in FIG. 2. The processor 210, provided as a portable electronic device or desktop computer, as examples, receives input data 220 from the wearer. The input 220 is data that includes a response by a wearer who is undergoing the analysis to a particular query. The query may be provided by another person or as output 230 provided by the portable electronic device or desktop computer. A query is a question, a statement, an image, or a selection of some type, or combinations thereof. Some or all of the input data 220 may be recorded and stored in memory 250, such as in database 270, or analyzed by logic/instructions 260. In some embodiments, only a portion of the input 220 or response data is included in an analysis or stored in memory 250. Some or all of the recorded data may be stored. Some or all of the recorded data may be transferred or transmitted to another device.

Some embodiments will include a non-transitory computer readable medium having computer program logic encoded thereon, in which the logic comprises instructions, which comprise output instructions for providing the queries as well as input instructions for receiving response data from the individual wearer or from an electronic device or medium. The computer program logic may also include analysis instructions for analyzing all or a portion of the response data as well as a second set of output instructions for providing additional output 230 as results of the analysis, including providing the identification factor. The instructions associated with the computer program logic may be stored locally in memory 250 or remotely (e.g., at a remote server). Input 220 and output 230 to and from the processor may be transmitted locally or remotely and may include an interface. The computer program logic may include a generator that introduces randomization to the first analysis or perception analysis, introducing unpredictability to the test.

For example, any of a number of queries (e.g., questions, statements, and/or images) may be randomly selected from a number of queries having the same weight or same value. In addition, any number of non-weighted queries may be introduced, at random, which do not form a part of the first analysis, but may provide other information or preferences related to the wearer or may simply be introduced to put the wearer as ease. Only the weighted queries will be evaluated in order to provide a first identification factor. Other evaluation means, in addition to formula (1), for providing a first identification factor include but are not limited to t-test, probability value test, Poisson distribution, derivation of correlation coefficients for each weighted query, and measuring for consistency of each question over a period of time and/or over a population of wearers.

In some embodiments the computer/processor described herein is an all-in-one electronic device capable of prompting, collecting, recording, assessing, transforming, and reporting as part of the first analysis. Such a device may also provide output to a designated server, printer, and/or display. A database housing any of the data may be a secured database, either as part of the computer/processing device or distinct from computer/processing device. An all-in-one electronic device may further comprise at least some or all of: a central processing unit (CPU), a graphic-user interface (GUI), a read-only memory (ROM), a random access memory (RAM), an electronic data storage device (e.g., hard disk), a circuit board, a cooling device (e.g., fan), a graphic accelerator chip, a communication board (e.g., a wireless communication board), a sound card, serial or parallel port, disk controllers and data bus controllers and connectors, and other electronic components typically associated with the building of a computing device.

Performing the first analysis may occur at a same location or near a same location as the location used to determine the first identification factor. In other embodiments, the performing of the first analysis and determining of the first identification factor occur at different locations. For example, data obtained from the first analysis may be configured to be delivered to another location, where the first identification factor is determined at the other location. For example, a wearer may be able to perform the first analysis online at one location (e.g., at home, in an office), and the identification factor may be provided to and/or calculated at a separate location or may be accessible only when at a separate location, such as an optometrist's office. The identification factor or the data used to calculate the first identification factor may, in some instances, be provided remotely. The delivery of data associated with the first analysis (e.g., the wearer's response) and/or the identification factor associated with the first analysis may be through an internet connection (wired or wireless) or through a storage medium used to record and store some or all of the data associated with the analysis and/or the identification factor when obtained, or any of the data may be delivered in writing, as examples. In some embodiments, the first analysis is performed online. In some embodiments, the first analysis is performed at a work station, such as, for example, a kiosk. In some embodiments, the first analysis is performed in an office setting, such as in an optometrist's office.

For identifying a second identification factor, a second analysis is performed. A second analysis is an objective analysis. The second analysis is generally a wavefront analysis. The wavefront analysis may obtain measurements based on Shack-Hartmann wavefront aberrometry. The analysis uses a sensor or array of apertures to measure the wavefront of the eye (emerging from the eye), including sphere, cylinder and the higher-order aberrations. This includes determining a wavefront shape by measuring the quality of a light beam as it passes through the eye. The distance between the wavefront surface refracted by an eye's optic and a reference plane located in the eye's entrance pupil is known as the wavefront error. A Shack-Hartmann data set is generally used and consists of a large array of numbers (wavefront errors) for different positions on the pupil plane. Any type of sensor may be used, including a lenslet array or suitable chart, grid, or the like with or without selective blocking or masking. As a whole, the entire data set collected is called the wavefront.

As described herein, the second analysis will generally include data comprising computer based measurements or gradings of the ocular surfaces, including the corneal curvature, refractive errors and aberrations, of both eyes. The second analysis may also include mesopic pupil size and wavefront optimization. While low order aberrations may be measured by either an automated refractor or a wavefront aberrometer, in which measurement obtained by the two methods generally correlate fairly well in sphere, cylinder and axis measurements, higher order aberrations may be better identified by a wavefront aberrometer. In one or more forms, an automated refractor or an aberrometer is used for the second analysis. In some embodiments, the aberrometer may be an instrument that combines features of an auto refractor and an aberrometer, and optionally has additional features, including those of a keratometer, pupilometer, topographer, retinoscopy, and/or tonometer, as examples. In some embodiments, the instrument used may be autorefractor keratometer, automated to detect optical power of each eye, their corneal curvature and regularity. In some embodiments, the instrument used is an autorefractor, keratometer, pupillometer, corneal topographer, and wavefront aberrometer.

Often, when an instrument for measurement is selected for the second analysis, it is preferable that the same instrument (or same type of instrument) be used for analysis of a number of individual wearers. This minimizes any differences in accuracy and repeatability of measurements in a wearer and between wearers. Ideally, the selected instrument uses a plurality of captured data and/or images to digitally map surface contours of each eye. In one or more embodiments, the instrument measures both higher and lower order aberrations. Lower order aberrations include myopia, hyperopia and astigmatism, as examples. Higher order aberrations include halos, starburst, glare, coma, trefoil, and quadrafoil, as examples. The instrument may include wireless, infrared remote, and/or keypad controls. The instrument may further include a display, such as a high contrast display, as well as quick access to the instrument settings. In addition, the instrument may be fully programmable. In some embodiments, the aberrometer is capable of auto aligning, auto tracking, and may include an auto chin rest, touch screen keyboard, and verification means upon making measurements. Data and images captured by the instrument are generally stored on a computer or processor, which is generally also capable of transforming the data and images and providing output of some or all of the data and/or images. The second analysis is generally performed in less than 40 minutes, or less than 30 minutes, or less than 20 minutes, or less than 15 minutes, or less than 10 minutes. In one or more embodiments, the data obtained from the first analysis may be combined with the data obtained from the second and/or third analysis, either in whole or in part. Data from the first, second and/or third analysis may be stored in a same or different database or in one or more data files stored on a computer or processor or in some accessible form of memory.

The second analysis provides the second identification factor. In some embodiments, the second identification factor is not obtained unless an individual wearer is suitable for wavefront analysis. In one or more embodiments, wavefront analysis is performed and considered suitable when an individual wearer presents a difference between auto refraction and wavefront refraction that is: (a) equal to or less than 0.5 diopter sphere or equal to or less than 0.5 diopter cylinder and (b) equal to or less than 10 degree axis. Thus, the second analysis may include both auto refraction and wavefront refraction. No specific order of the analyses is required. In the individual wearers, when the second analysis or wavefront analysis is performed, those wearers who meet the preceding (a) and (b) criteria and who have a second identification factor value at or within the predetermined value for the second analysis are selected, in which the predetermined value includes a root mean square (RMS) value lower than 0.3 diopter, or a root mean square (RMS) value lower than 0.2 diopter in both eyes. Thus, in one embodiment, an individual wearer who undergoes wavefront analysis, as well as autorefraction having met the criteria (a) and (b), is selected when identified as having a second identification factor that is at or within the predetermined value. In some embodiments, an individual wearer is eligible for wavefront analysis after having been identified by criteria (a) and (b), and is selected as having a second identification factor that is at or within the predetermined value after a total RMS wavefront error is obtained from the wavefront analysis. The total RMS value provides an overall assessment (e.g., magnitude) of all aberrations, e.g., the eye's refractive errors, including sphere, cylinder, and higher-order aberrations. Generally, the higher the RMS value the greater the number of aberrations, because it shows how much a value deviates from the mean or average.

Quantitative comparisons between different eyes and conditions are usually made using RMS. In order to measure RMS, for each type of aberration the difference between the aberration and mean value is squared and averaged across the pupil area.

In one embodiment, a wavefront analysis is performed without any pupil dilation. In some embodiments, wavefront data will be obtained with only a single pupil diameter, such as 4 mm. In some embodiments, wavefront data will be obtained at more than one pupil diameter, such as at two different diameters. Pupil diameters will typically range from about 2 mm to about 8 mm. Any pupil dilation is typically in the presence of a dilator, such as tropicamide or neosynephrine, or combinations or other suitable agents and their equivalents. Generally, more than one measurement is taken with each eye. In some embodiments, several measurements are obtained and the values are averaged. This is also useful to improve reproducibility in the system. From the wavefront data, the RMS wavefront error is obtained. If more than one pupil diameter is used, then the RMS wavefront error is obtained for each pupil diameter. Total RMS is then obtained. The RMS error is generally obtained by a computer or processor programmed to compute the RMS error. In one or more forms, the RMS error is described by the overall magnitude of all the refractive errors (lower and higher order, or sphere, cylinder and higher order aberrations). The RMS may be recorded and measured to a scale of 0.01 microns. An individual wearer having an RMS error at or within a predetermined value is then selected. In one or more forms, the predetermined value is a total RMS error at or less than 0.3 in each eye. In some forms the predetermined value is an RMS error at or less than 0.2 in each eye. In some embodiments, an individual wearer having an RMS above 0.3 and up to about 0.47 in each eye may also be dispensed with a higher order corrective ophthalmic lens as described herein.

Performing the second analysis may occur at a same location or near a same location as the location used to determine the second identification factor. In some embodiments, the second analysis is performed in the same location or near the same location as the first analysis. However, this is not necessary. For example, data obtained from the first analysis may be configured to be delivered to another location, where the second identification factor is determined at the other location. Similarly, data obtained from the second analysis may be configured to be delivered to another location, where the second identification factor is determined at the other location. The delivery methods may be through an internet connection (wired or wireless), or through a storage medium used to store some or all of the data associated with the first and/or second analysis, or in writing, as examples. In some embodiments, the second analysis is performed at a work station, such as for example, a kiosk. In some embodiments, the second analysis is performed in an office setting, such as in an optometrist's office.

The third identification factor is identified by performing a third analysis. The third analysis is a subjective refraction analysis. The subjective analysis uses a phoropter or other like instrument or device for measuring refraction of each eye separately and subjectively. With the subjective analysis, the sphere and cylinder changes are in steps of 0.12 diopter, or in steps of 0.125 diopter, rather than the typical 0.25 diopter or 0.5 diopter changes that are currently (traditionally) being made. In some embodiments, the changes are in increments, in any number or range between about 0.01 and about 0.17 diopter. In some embodiments, the changes are in increments, in any number or range between about 0.01 and about 0.125 diopter. In some embodiments, the changes are in increments, in any number or range between about 0.12 and about 0.17 diopter. In some embodiments, the changes are in increments, in any number or range between about 0.12 and about 0.125 diopter. Thus, the third analysis requires finer parameters, which manifest in a higher level of correction of visual acuity for an individual wearer when dispensed a higher order corrective ophthalmic lens and described herein. An individual wearer that perceives cylinder changes at or within a predetermined value is then selected. In the third analysis, the predetermined value for the third identification factor is perceiving a cylinder change of 0.12 diopter or less. In some embodiments, the predetermined value for the third identification factor is perceiving a cylinder change of 0.125 diopter or less. In some embodiments, the predetermined value for the third identification factor is perceiving a cylinder change in a range of between about 0.01 diopter and 0.17 diopter, or is perceiving a cylinder change of 0.17 diopter or less.

Performing the third analysis may occur at a same or near a same location as the location used to determine the third identification factor. In other embodiments, the performing and determining occur at different locations. For example, data obtained from the third analysis may be configured to be delivered to another location, where the third identification factor is determined at the other location. The delivery method may be through an internet connection (wired or wireless), or through a storage medium used to store some or all of the data associated with the third analysis, or in writing. Data collected from the first analysis and/or second analysis may be obtained and evaluated at the same location or a different location than the third analysis. Similarly, data obtained from any of the first analysis, the second analysis and/or third analysis may be configured to be delivered to another location, where the identification factors are determined at the other location. In some embodiments, some or all of the third analysis is performed at a work station. In some embodiments, the third analysis is performed in an office setting, such as in an optometrist's office. In some embodiments, at least the second analysis and third analysis are performed in the same general location. In some embodiments, at least the second analysis and third analysis may be performed in an office setting, such as in an optometrist's office.

Any of the first analysis, second analysis and/or third analysis may be semi-automated or automated, such that analysis continues in a timed or predetermined sequence, or may be manually driven, or some combination thereof.

One or more of the first analysis, second analysis and/or third analysis comprises a computer/processor or computing device, with an input means and a display or output means. The computing device further comprises a processing unit and a computer readable medium. Generally, the computing device is a general purpose computer or digital signal processor ("DSP") configured by a computer program stored therein. The computer program may be stored in a computer readable storage medium, such as, but not limited to, any type of disk, including but not limited to floppy disk, optical disk, CD-ROM, magnetic-optical disk, read-only memory (ROM), random access memory (RAM), electrically programmable read-only memory (EPROM), electrically erasable and programmable read only memory (EEPROM), magnetic or optical card, or any other type of media suitable for storing electronic instructions, and as they are made available, and capable of being coupled to a computer system bus. The computing device may execute an operating system on the computer-readable medium, such but not limited to as Microsoft® Windows 9x, OS, Me, XP, Windows CE, UNIX®, LINUX®, Pocket® PC OS or the like, as they are made available. Also included in the computer-readable medium is a set of instructions for performing functions related to the analysis and/or the operation of the computing device. The computing device may include but is not limited to a personal computer, handheld device, mobile computing device, personal digital assistant (PDA), mobile phone, pager, and microprocessor-based wired or wireless information device, including devices not listed as they are made available for use in the manner described. Often, the input/output means for interacting with the analysis are embodied within the computing device, such as the graphical user interface, an LCD display, a touch screen display, buttons, a mouse, a curser, a microphone, and a speaker. Alternatively, an input and/or output means can be added onto any of the aforementioned devices as a peripheral. A network may be coupled to the computing device via a wired or wireless connection, such as Ethernet, IEEE 1394, TDMA, CDMA, GSM, PTSN, ATM, ISDN, 802.1X, USB, Parallel, Serial, UART (RS-232C), as representative and non-limiting examples.

For example, any one or more, or all of the first, second and third analysis may include a computer/processor to administer or perform the analysis and/or to collect data obtained from the analysis. When an analysis is administered or performed by a computer/processor, specific software programmed to perform the analysis will be used, and some or all of the analysis may be provided on one or more data screens. The software will also produce certain data screens to input information about the individual wearer. When a processor/computer is used to collect data, it can collect the data in defined data sets. Additionally, in any one or more of the first, second and third analysis, an individual wearer or a support personnel may interface with the computer/processor that may be used at a desk, in an office setting, or in an exam room, as examples. The individual wearer/support personnel interface may be through a computer mouse, a keypad, a notebook, a tablet computer, a touch screen, voice recognition, each of which is provided as a suitable and representative example. The data may be stored locally on the computer/processor (e.g., hard drive), on a removable storage device, or on a central storage receiver. Data may also be transferred as output or to another computer/processor or to a central system. Output may be provided locally or after transferring data. Reports may be generated by suitable software and hardware. A report may be specific to an individual wearer, to any of the first, second and/or third analysis (e.g., for one or a number of individual wearers), by date, etc. A report may be numeric, graphical, include images and various combinations thereof. For example, to generate a report for an individual wearer, software may be programmed to select data for the individual wearer, or to a specific identification (e.g., user ID or user information) associated with the individual wearer, such as when there are privacy concerns. A report may include all data or a subset of data, or a comparison of data, by appropriate selection.

In one or more embodiments, an instrument that performs the semi-automated or automated third analysis may be combined with the instrument used to perform the second analysis. In one or more embodiments, data obtained from the third analysis may be combined with data obtained from the second analysis, either in whole or in part. In one or more embodiments, data obtained from the third analysis may be combined with data obtained from the second analysis and the first analysis, either in whole or in part. For example, an instrument used for the third analysis may directly incorporate data from an instrument used for the second analysis. In some embodiments, a system used for the second analysis may also include an instrument for performing the third analysis, such that the system comprises a device having an instrument for performing at least the second analysis and an instrument for performing at least the third analysis. In such a system, at least some of the instrument for performing the second analysis and some of the instrument for performing the third analysis may be the same. Alternatively, the system may include a first instrument for performing the second analysis and a second instrument for performing the third analysis. Such a system will generally be operably linked, such that the first instrument and second instrument are communicatively cooperative or communicatively coupled. In some embodiments, a system includes an instrument for performing the first analysis, an instrument for performing the second analysis, and an instrument for performing the third analysis. In such a system, some or all of the instruments may be capable of performing the first, second and third analysis. Alternatively, in such a system, the system may include one instrument capable of performing one or more of the first, second and third analysis, or at least two of the analyses. In any such system, the instruments may be operably linked and/or communicatively coupled.

Generally, the determination of the first identification factor, the second identification factor and the third identification factor are obtained sequentially. However, the determination of the first identification factor and either the second or third identification factor may otherwise be obtained at about the same time. In one or more embodiments, the first analysis may be obtained and/or performed online or on a computer or computer-assisted device. In some embodiments, some or all of the first, second and third analysis are performed in a single location. In one or more embodiments, performing the first analysis, the second analysis and the third analysis occur in a period of less than 2 hours, or less than 1.5 hours or less than 1 hour or less than 45 minutes. In one or more embodiments, obtaining the first identification factor (or data about the first identification factor), the second identification factor (or data about the first identification factor), and the third identification factor (or data about the first identification factor) occur in a period of less than 2 hours, or less than 1.5 hours or less than 1 hour or less than 45 minutes, or less than thirty minutes, or less than twenty minutes, or less than 10 minutes. In one or more embodiments, the determination of the first identification factor, the second identification factor and/or the third identification factor occur in a period of less than 2 hours, or less than 1.5 hours, or less than 1 hour, or less than 45 minutes, or less than thirty minutes, or less than twenty minutes, or less than 10 minutes.

In one or more forms, wavefront aberrometry data, which is data obtained from the second analysis, may be considered in combination or in context with refraction data obtained from the third analysis. This provides higher order corrections to the spherocylindrical prescription for a higher order corrective ophthalmic lens. The higher order corrections are prescribed at least to the nearest 0.125 diopter, or at least to the nearest 0.12 diopter, or to a number or range to the nearest 0.125 diopter or less, or to a number or range to the nearest 0.12 diopter or less. The higher order corrections may be values obtained from at least the subjective analysis. The higher order corrections may be values obtained from at least the objective analysis. Thus, the higher order corrections may be prescribed to the nearest value or in a range of values between about 0.01 diopter and 0.17 diopter, or may be prescribed to the nearest value or in a range of values between about 0.17 diopter and less, or may be prescribed to the nearest value or in a range of values between about 0.12 and 0.125 diopter, or may be prescribed to the nearest value or in a range of values between about 0.01 and 0.12 diopter, or may be prescribed to the nearest value or in a range of values between about 0.01 and 0.125 diopter, or may be prescribed to the nearest value or in a range of values between about 0.12 and 0.17 diopter.

In addition, any number of optional analyses may also be conducted for the benefit of the individual wearer. These include but are not limited to position of wear tests, postural tests or center of rotation tests of the head, wavefront optimizations at pupil sizes from 2 to 8 mm, and additional higher order RMS calculations for identifying higher order refractive readings.

With the methods described herein, higher order corrective ophthalmic lenses based on data obtained from at least the second and/or third analysis are provided to the selected individual wearer. In some embodiments, corrective lenses provided to the selected individual wearer are based on data obtained from both the second analysis and the third analysis. The selected individual wearer is one identified as having the first identification factor, the second identification factor and the third identification factor, wherein the first, second and third identification factors are all at or within the predetermined values provided and described herein for each of the identification factors.

As described herein, based upon the aforementioned analyses, an ophthalmic lens prescribed with the wearer specific higher order diopter corrections is manufactured for the selected individual wearer. Any corrective ophthalmic lens may be provided to the selected individual wearer, including but not limited to single vision lens, progressive lens, divergent lens, convergent lens, toric lens, adjustable focus lens, intraocular lens, plano lens, multi-focal lens and combinations thereof. The lens may have any of a number of optical profiles, including biconvex, plano convex, concave-convex, meniscus, plano concave and biconcave. The lens may be configured as a spectacle lens for a frame. The lens may also be configured as a contact lens. The lens may also be configured as a visor. For a spectacle frame lens or a contact lens, in which there are two lenses, one for each eye, the two lenses do not have to have the same prescription. For manufacturing the wearer-specific corrective ophthalmic lens, the digital data from the second analysis or wavefront analysis may also be used to provide a so-called digital lens as a more accurate complement to the curvature and aberrations of the eye. For example, the higher order aberrations identified for the individual wearer in the second analysis are then provided to the surface of the ophthalmic lens during the manufacturing process.

Figure 4:
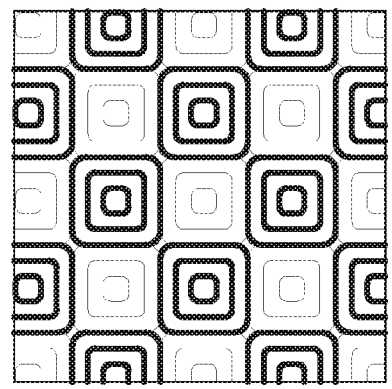
FIG. 4 depicts a representative reading card used for analyzing an individual's quality of vision as described herein.

When the ophthalmic lens is formed and available to the selected individual wearer, a fourth analysis is performed. The fourth analysis ensures that the selected individual wearer has improved quality of vision and/or visual comfort when wearing the wearer-specific corrective ophthalmic lens. In various embodiments, the fourth analysis includes viewing one or a plurality of reading cards as depicted in FIGS. 4 and 6. FIG. 4 is an example of a reading card that may be used to analyze an individual's contrast sensitivity and/or color perception. FIG. 6 depicts a more detailed reading card, which an individual may view in order to analyze their perception of various shades or textures 602-608 on the reading card. From the fourth analysis, a fourth identification factor is identified, which includes the ability to identify, with better clarity, contrast, sharpness and/or color, the one or plurality of reading cards. In one or more embodiments, the fourth analysis is performed when the wearer is fitted with the new wearer-specific corrective lens prepared as described herein, as compared with being fitted with the wearer's old or previously worn lens. When no previous lens had been prescribed to or had been worn by the wearer, the fourth analysis is performed when the wearer is fitted with the new wearer-specific corrective lens prepared as described herein, and is compared with data obtained when having no fitted lens (no lens). The fourth analysis may also include a monocular and binocular visual acuity analysis with and without the new lens, performed by an optometrist or an ophthalmologist or may be an analysis of a type that does not have to be performed by an optometrist or an ophthalmologist. The fourth analysis may include providing reading cards (e.g., graphics, numbers, or images) and/or questions used during the first analysis, thereby repeating at least some of the visual analysis performed during the first analysis, obtaining a predetermined value in the same manner as was obtained in the first analysis, and comparing the first predetermined value with the fourth predetermined value, such that the predetermined value for the fourth identification factor is an improvement in response to visual clarity, contrast, sharpness and/or color, and/or is an improvement in the recognition of visual changes, as compared with the response obtained from the first analysis. The fourth analysis may also include a questionnaire to assess wearer satisfaction. The fourth analysis may further comprise a follow-up analysis, comprising a visual acuity analysis, assessment of visual performance, and/or a questionnaire, or some combination thereof, which may also be used to assess wearer satisfaction.

Figure 3:
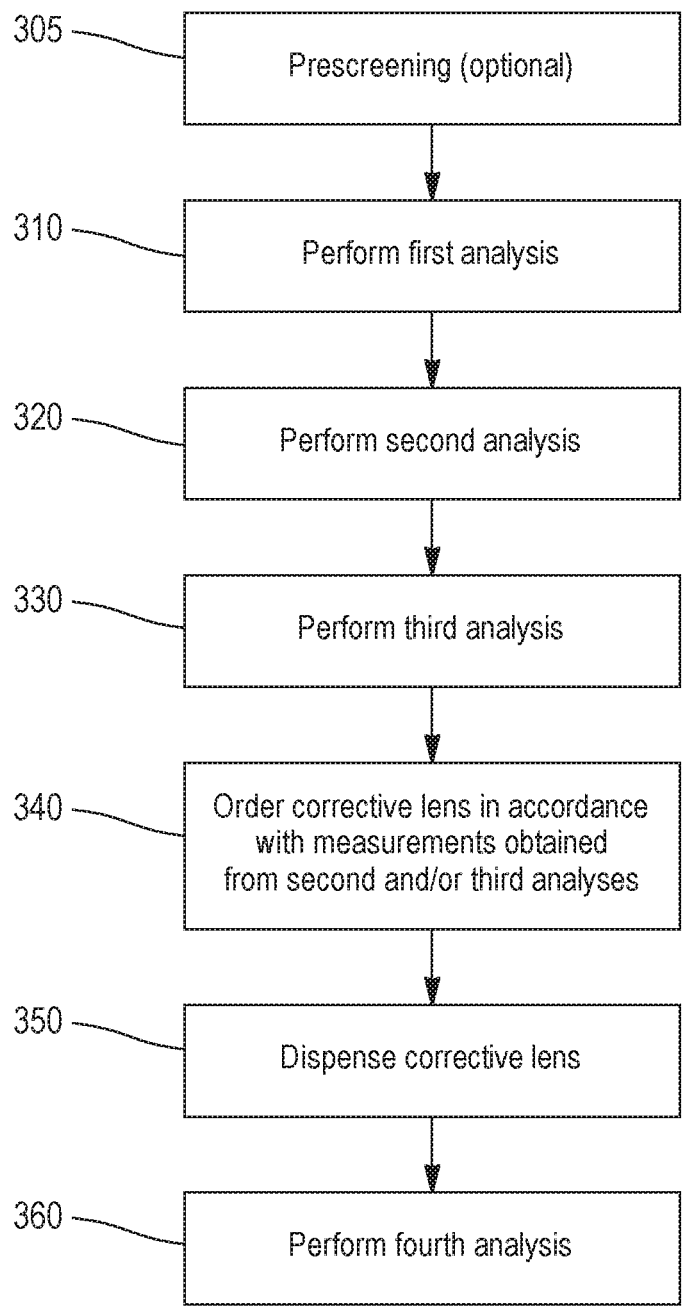
FIG. 3 depicts another representative method for providing higher order corrective lenses based on the steps of the one or more methods as described herein.

As exemplified by FIG. 3, an individual wearer recognized in accordance with the methods and systems described herein will typically undergo the following: a first analysis as illustrated in block 310, a second analysis as illustrated in block 320 and a third analysis as illustrated in block 330. Optionally, a prescreening step may be performed at block 305. The prescreening may be one that provides predetermined limitations, such as limiting age related ocular changes (e.g., based on age, disease, visual acuity, or other measure of visual performance), and/or may exclude other preconditions (e.g., disease, or prior prescriptions that do not have a sphere of +3.0 to −4.00 DS and/or sphero-cylindrical combination power in any meridian that does not exceed −4.50 D). In one embodiment, upon completion of these analyses (block 310, 320 and 330, with or without block 305), in any of a number of orders (as previously outlined), and only when, upon completion of each analysis having the identification factors identified at or within the predetermined values, a prescription is prepared with block 340 for the selected individual wear in accordance with measurements obtained from either or both the second and third analysis. In some embodiments, a precise, wearer-specific corrective ophthalmic lens is ordered in block 340 for the selected individual wearer in accordance with specific individual measurements obtained from at least the third analysis, and which may also include measurements obtained from the second analysis. The prescription may then be filled in accordance with practices known in the relevant art. The ordered lens, when precisely manufactured, is then dispensed in block 350. Upon dispensing of the wearer-specific lens, the individual wearer undergoes the fourth analysis in block 360. It is noted that the identification factors do not have to be identified in any order or with any specific timing; however, in one embodiment, all of the identification factors must be assessed and determined to be at or within their predetermined value before dispensing a wearer-specific corrective ophthalmic lens. In an alternative embodiment, all of said identification factors may be assessed and a specific corrective lens will be dispensed when only some of the identification factors are at or within their predetermined value. In still further embodiments, not all of said identification factors are assessed and a specific corrective lens is dispensed when only some or none of the identification factors are at or within their predetermined value. Preferably, the selected wearer will, upon performing the fourth analysis, have an identification factor that is at or within the predetermined value for the fourth identification factor. A selected individual wearer who does not provide a fourth identification factor at or within the predetermined valued may still and may likely express satisfaction with the corrective ophthalmic lens and may keep the corrective ophthalmic lens.

Data obtained from the first analysis may be combined with the data obtained from the second analysis, the third analysis and the fourth analysis, either in whole or in part. Data from the first, second, third and/or fourth analysis may be stored in a same or different database or in one or more data files stored on a computer or processor or in some accessible form of memory, or in writing.

Any combination of steps of the methods described herein may be provided on a computer program product comprising one or more stored sequence of instruction that is accessible to a processor and which, when executed by the processor, causes the processor to carry out the steps. In addition, a computer-readable medium may be provided that carries out the sequence of instructions of the computer program product.

The described methods and systems manage both high order aberrations while providing a finer correction for an ophthalmic lens that is specific to a selected individual wearer. This is important when manufacturing a progressive lens for an individual wearer who is capable of correcting lateral image blur, which may otherwise adversely affect the success of the adaptation process, when not adequately corrected. The described methods and system also allow for an ability to provide a means for discriminating different textures at different levels of luminosity, the levels having a direct relationship with second order vision.

In some embodiments, the individual wearer is any wearer. In some embodiments, the individual wearer is a new wearer. In some embodiments, the individual wearer is an adapted spectacle wearer. In some embodiments, the individual wearer is who does not exhibit age related ocular changes. In some embodiments, the individual wearer may have age related ocular changes. In some embodiments, the individual wearer presents or had previously presented a visual acuity of at least 20/20 in each eye with conventional spectacle refraction analysis. In some embodiments, it may be preferable that a recent or previous spectacle prescription have a sphere value of between +3.00 to −4.00 DS and that the sphero-cylindrical combination power in any meridian does not exceed −4.50 D.

In a first example, individual wearers were each individually provided the questionnaire of TABLE 2 in an office setting. A first identification factor was evaluated in accordance with formula (1) for each individual wearer. Individual wearers having a first identification factor of 3.5 or below were selected. The selected individual wearers were measured for a second identification factor using a refractive machine/corneal analyzer by Nidek, Inc., OPD-Scan III, in an office setting. Individual wearers evaluated by the analyzer (and for the second identification factor) were those in which a difference between auto refraction and wavefront refraction was: (a) equal to or less than 0.5 diopter sphere or equal to or less than 0.5 diopter cylinder and (b) equal to or less than 10 degree axis. In the individual wearers, those having an RMS lower than 0.2 diopters in both eyes were selected. The selected individual wearers were then evaluated for a third identification factor. Individual wearers selected were those recognizing 0.12 diopter step changes monocular and binocularly in the subjective or third analysis. The subjective analysis was performed in an examination room with lights on using an automated and programmable refraction system by Marco, TARS-5100. The analysis included evaluation of pupillary distance, visual acuity, sphere refinement (with or without cylinder axis and power refinement), binocular vision and/or binocular balance (with +0.50 fog or binocular duo chrome test). For the selected individual wearers, a single vision or multisession ophthalmic spectacle lens was manufactured, as Varilux SV 360, Varilux Physio DRx™, Varilux Physio Short DRx™, respectively. It is understood, however, that another spectacle lens may be readily manufactured in accordance with the needs of the selected individual wearer. Further, another type of lens may be manufactured in accordance with the needs of the selected individual wearer. Initial studies performed on 18 individual wearers showed that utilizing the exemplary system and method to manufacture each new wearer-specific corrective ophthalmic spectacle lens provided a new individualized ophthalmic lens that was considered to have more vivid color and detail, with superior clarity in low light conditions, and sharper vision across the lens, and a wider field of vision. All individual wearers chose to continue wearing their new wearer-specific corrective ophthalmic spectacle lens and would recommend the system and process as well as the lens produced therefrom to others, including relatives and friends.

Figure 5:
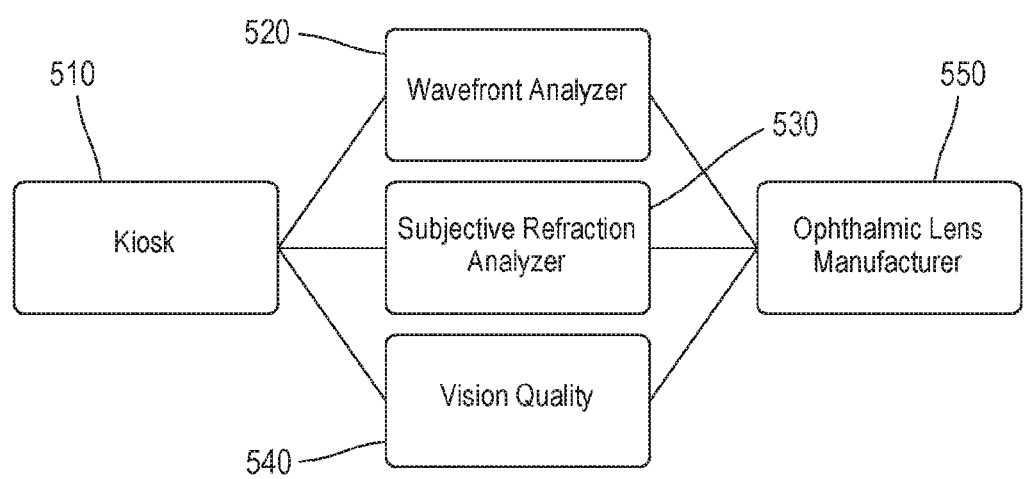
FIG. 5 depicts a representative system for identifying identification factors and selecting an individual wearer based on the steps of the one or more methods described herein.

A representative system is depicted in FIG. 5, which shows a work station, such as a kiosk 510 at which a first analysis of visual perception is performed. The kiosk may be, for example, a workstation at home or in an office setting, such as in an optometrist's office. A Wavefront Analyzer 520 for performing a second analysis and a means for subjectively analyzing and performing a third analysis 530, which may include any Subjective Refraction Analyzer, or a hand-held lens, or a portable or mobile device (e.g., eye tool for refractive assessment), may be located in an office setting, such as an optometrist's office, or in a medical setting. The location for performing the second analysis and the third analysis may be the same or different (e.g., different room or different building). In some embodiments, a device may include components that are capable of performing a first analysis and a second analysis. In some embodiments, a device may include components that are capable of performing a first analysis and a second analysis and a third analysis. In some embodiments, a device may include components that are capable of performing a second analysis and a third analysis. An Ophthalmic Lens Manufacturer 550, which obtains data, generally from one or both of the analyzer 520 and the analyzer 530, is often located away from the office. The individualized wearer-specific corrective ophthalmic lens produced by the Ophthalmic Lens Manufacturer 550 is generally dispensed in an office setting or medical setting, which is often where Vision Quality 540, as the fourth analysis, is performed. However, Vision Quality 540 may also be performed at home or at another alternative location. Any of the instruments associated with the kiosk 510, analyzer 520, analyzer 530, manufacturer 550, and vision quality 540 may be communicatively coupled or operatively coupled with one another (wired or wirelessly and/or via a network).

The embodiments disclosed above are illustrative only, as the methods and compositions described herein may be modified and practiced in different but equivalent manners apparent to those skilled in the art having the benefit of the teachings herein. It is, therefore, evident that the embodiments disclosed above may be altered or modified and all such variations are considered within the scope of the present invention. The various elements or steps according to the disclosed elements or steps can be combined advantageously or practiced together in various combinations or sub-combinations of elements or sequences of steps to increase the efficiency and benefits that can be obtained from the invention.

The words or terms used herein have their plain, ordinary meaning in the field of this disclosure, except to the extent explicitly and clearly defined in this disclosure or unless the specific context otherwise necessitates a different meaning.

If there is any conflict in the usages of a word or term in this disclosure and one or more patent(s) or other documents that may be incorporated by reference, the definitions that are consistent with this specification should be adopted.

The words "comprising," "containing," "including," "having," and all grammatical variations thereof are intended to have an open, non-limiting meaning. For example, a composition comprising a component does not exclude it from having additional components, an apparatus comprising a part does not exclude it from having additional parts, and a method having a step does not exclude it having additional steps.

The indefinite articles "a" or "an" mean one or more than one of the component, part, or step that the article introduces.

Whenever a numerical range of degree or measurement with a lower limit and an upper limit is disclosed, any number and any range falling within the range is also intended to be specifically disclosed. For example, every range of values (in the form "from a to b," or "from about a to about b," or "from about a to b," "from approximately a to b," and any similar expressions, where "a" and "b" represent numerical values of degree or measurement) is to be understood to set forth every number and range encompassed within the broader range of values, including the values "a" and "b" themselves. Terms such as "first," "second," "third," etc. may be arbitrarily assigned and are merely intended to differentiate between two or more components, parts, or steps that are otherwise similar or corresponding in nature, structure, function, or action. For example, the words "first" and "second" serve no other purpose and are not part of the name or description of the following name or descriptive terms. The mere use of the term "first" does not mean that there is a required "second" similar or corresponding component, part, or step. Similarly, the mere use of the word "second" does not mean that there must be any "first" or "third" similar or corresponding component, part, or step. Further, it is to be understood that the mere use of the term "first" does not mean that the element or step be the very first in any sequence, but merely that it is at least one of the elements or steps. Similarly, the mere use of the terms "first" and "second" does not mean any sequence. Accordingly, the mere use of such terms does not exclude intervening elements or steps between the "first" and "second" elements or steps.

It will be appreciated that one or more of the above embodiments may be combined with one or more of the other embodiments, unless explicitly stated otherwise. The invention illustratively disclosed herein suitably may be practiced in the absence of any element or step that is not specifically disclosed or claimed. Furthermore, no limitations are intended to the details of construction, composition, design, or steps herein shown, other than as described in the claims.

The invention claimed is:

1. A method for providing a prescription for a corrective ophthalmic lens for a selected individual wearer, the method comprising:

using a first instrument, identifying in a first analysis a first identification factor from a plurality of parameters for evaluating an individual wearers' level of perception and control;

using a second instrument, identifying in a second analysis a second identification factor, wherein the second instrument includes equipment for objectively measuring refractive error in an eye, wherein the second analysis is performed when the first identification factor is within a predetermined value;

using a third instrument, identifying in a third analysis a third identification factor, wherein the third instrument includes equipment for subjectively evaluating refraction in an eye and refraction is evaluated using an incremental change that is lower than 0.20 diopter, or is in a range between about the nearest 0.01 diopter and about the nearest 0.20 diopter, wherein the third analysis is performed when the second identification factor is within a predetermined value; and generating a prescription based on the refraction obtained from at least one of the second instrument and the third instrument, wherein the prescription includes at least one correction that is to the nearest 0.20 diopter, or is in a range between about the nearest 0.01 diopter and about the nearest 0.20 diopter.

2. The method of claim 1, further comprising after dispensing the prescription, identifying in a fourth analysis a fourth identification factor, wherein the fourth analysis includes a visual acuity assessment.

3. The method of claim 2, further comprising providing an indicator of performance criterion.

4. The method of claim 1, wherein the plurality of parameters are questions provided in a questionnaire.

5. The method of claim 1, wherein the refractive error is one or more of a total root mean square of at least about 0.3 diopter or less in each eye and at least about 0.2 diopter or less in each eye.

6. The method of claim 1, wherein the refractive error is measured using a wavefront aberrometer.

7. The method of claim 1, wherein the first identification factor is associated with having self confidence and organizational skills.

8. The method of claim 1, wherein the second identification factor of the wearer is identified when the wearer presents a difference between auto refraction and wavefront refraction that is (i) equal to or less than 0.5 diopter sphere or equal to or less than 0.5 diopter cylinder and (ii) equal to or less than 10 degree axis.

9. The method of claim 1, further comprising:
determining a sensitivity factor for the wearer, the sensitivity factor being indicative of the wearer's ability to perceive a change lower than 0.25 diopter, where the higher the sensitivity factor, the more suitable a wearer is for an enhanced corrective ophthalmic lens.

10. The method of claim 9, wherein the first instrument comprises a wavefront aberrometer or an autorefractor.

11. The method of claim 9, wherein one of the plurality of parameters is related to a pupil diameter of the wearer.

12. A system for evaluating a wearer in need of a corrective ophthalmic lens, the system comprising:
a kiosk for performing a first analysis by evaluating a wearers' level of perception and control, and for providing information about the personal perception and control of the wearer, in the first analysis a first identification factor is identified from a plurality of parameters for evaluating the wearers' level of perception and control;

a first equipment for performing a second analysis by objectively measuring a wavefront of each eye of the wearer and for providing information about the wavefront, in the second analysis a second identification factor is identified, the second analysis being performed when the first identification factor is within a predetermined value; and a subjective refraction analyzer for performing a third analysis by measuring subjectively refraction in each eye of the wearer and for providing information about the refraction, in the third analysis a third identification factor is identified, the third analysis being performed when the second identification factor is within a predetermined value, wherein the refraction is evaluated using an incremental change that is lower than 0.20 diopter, or is in a range between about the nearest 0.01 diopter and about the nearest 0.20 diopter.

13. The system of claim 12, wherein the system determines that a wearer is in need of the corrective ophthalmic lens when the information about the personal perception and control of the wearer indicates the wearer as having one or more of self confidence and organizational skills, and when the information about the wavefront provides a total root mean square value of 0.3 diopter or less, and when the wearer perceives the incremental change that is lower than 0.20 diopter, or is in a range between about the nearest 0.01 diopter and about the nearest 0.20 diopter.

14. The system of claim 12, wherein one or more of the kiosk, the first equipment, and subjective refraction analyzer are operably linked.

* * * * *